(12) United States Patent
Igarashi et al.

(10) Patent No.: US 7,018,359 B2
(45) Date of Patent: Mar. 28, 2006

(54) INNER PRESSURE INDICATOR OF CUFF

(75) Inventors: Daisuke Igarashi, Yamagata-ken (JP);
Akira Sato, Yamagata-ken (JP);
Takeshi Ohgawara, Tokyo (JP)

(73) Assignee: Koken Co., Ltd., Tokyo (JP)

( * ) Notice: Subject to any disclaimer, the term of this patent is extended or adjusted under 35 U.S.C. 154(b) by 0 days.

(21) Appl. No.: 10/161,646

(22) Filed: Jun. 5, 2002

(65) Prior Publication Data

US 2002/0157665 A1     Oct. 31, 2002

Related U.S. Application Data

(63) Continuation of application No. 09/599,527, filed on Jun. 23, 2000, now abandoned.

(30) Foreign Application Priority Data

Jun. 25, 1999    (JP) .................................. 11-180430
Jun. 7, 2000     (JP) ............................. 2000-169999

(51) Int. Cl.
*A61M 29/00*    (2006.01)

(52) U.S. Cl. .............................. 604/100.01; 604/97.03; 128/205.23

(58) Field of Classification Search ........... 128/207.14, 128/207.15, 207.16, 205.23; 116/210, 218, 116/ 220,200, 201, 266, 270, 273, 277, DIG. 9; 604/97.01, 97.03, 99.01, 99.02, 99.03, 99.04, 100.01, 100.02, 100.03

See application file for complete search history.

(56) References Cited

U.S. PATENT DOCUMENTS

| 3,905,361 | A | * | 9/1975 | Hewson et al. ......... 128/202.16 |
| 4,114,458 | A | * | 9/1978 | Alinari ..................... 73/729.1 |
| 4,331,155 | A | * | 5/1982 | Sacks ........................ 600/499 |
| 4,468,226 | A | * | 8/1984 | Kurtz et al. ................ 604/321 |
| 4,501,273 | A | * | 2/1985 | McGinnis ............. 128/207.15 |
| 4,617,015 | A | * | 10/1986 | Foltz .................... 604/100.01 |

* cited by examiner

*Primary Examiner*—Glenn K. Dawson
*Assistant Examiner*—Darwin P Erezo
(74) *Attorney, Agent, or Firm*—Sherman & Associates

(57) ABSTRACT

The present invention is an inner pressure indicator of a cuff comprising, a housing possessing on one end an opening that can connect to a cuff inflating tube of a tracheostomy tube with a cuff or of an endotracheal tube and on the other end of said housing possessing an opening to which a valve that prevents the reduction of inner pressure is equipped with, said housing is characterized by being equipped with an inner pressure indicating device of cuff and also the inner pressure of the cuff can be regulated by said opening with a valve by way of said inner pressure indicating device of the cuff.

6 Claims, 3 Drawing Sheets

INNER PRESSURE INDICATOR OF CUFF

CROSS REFERENCE TO RELATED APPLICATION

This application is a continuation of application Ser. No. 09/599,527, filed Jun. 23, 2000, now abandoned.

BACKGROUND OF THE INVENTION

1. Field of the Invention

The present invention relates to an inner pressure indicator of cuff attached to a tracheostomy tube with a cuff or a endotracheal tube with a cuff that are used for the emergency or long term breathing regulation, for the breathing regulation of an unconscious patient or for the breathing regulation used at general anesthesia. Especially, the present invention relates to an inner pressure indicator, which indicates not only the inner pressure of a cuff attached to a tracheostomy tube with a cuff or an endotracheal tube with a cuff but also regulates inner pressure of the cuff.

2. Description of the Prior Art

Usually, for the purpose of emergency or long term breathing regulation, for the breathing regulation of an unconscious patient or for the purpose to maintain trachea line at general anesthesia, various kinds of endotracheal tubes to be inserted into trachea from larynx or tracheostomy tubes to be inserted in the incised part of trachea have been developed. Among these tubes, a tracheostomy tube with a cuff or an endotracheal tube with a cuff that use a cuff of double tube structure are already developed. These kinds of tracheostomy tube with a cuff or endotracheal tube with a cuff can effectively prevent the air leaking from the gap between tube and trachea or the flowing in of saliva or vomited substance into trachea by the presence of a cuff. The most important point of said tracheostomy tube with a cuff or said endotracheal tube with a cuff is to regulate the inner pressure of cuff, and when the inner pressure of cuff is too low, the purpose of the cuff cannot be fully achieved, on the contrary, when the inner pressure of cuff is too high, it oppresses vascular in tracheal mucous membrane and makes trachea ischemic condition, and causes ulcer, bleeding and a granuloma further causes tracheal-stenosis or tracheo-malscia after the removal of the tube. In general, for the purpose to prevent the occurrence of said problems, it is desirable to maintain the inner pressure of a cuff within 25–30 mmHG. In the present invention, the inner pressure of a cuff is indicated by gage pressure, and gage pressure can be calculated by subtracting the atmosphere pressure (760 mmHG) from absolute inner pressure of cuff. At the actual use of these tubes by connection to a breathing device, usually the pressure of 100 mmHg is temporarily added to a cuff to confirm that there is no air leak from the breathing device. And at this procedure, it is important to regulate the inner pressure of the cuff not abnormally high pressure to be added.

Usually, in the actual use of a tracheostomy tube with a cuff or a endotracheal tube with a cuff, for the purpose to regulate the inner pressure of the cuff, following method is carried out. That is, air or physiological salt solution is poured into the cuff and inflate the cuff by a syringe, then the syringe is removed from the tube, the inner pressure of the cuff is measured by a pressure gage and the inner pressure of the cuff is regulated. Or, by regulating the amount of air at the inflation procedure of the cuff, the inner pressure of the cuff is adjusted. As mentioned above, in a case of the conventional tracheostomy tube with a cuff or endotracheal tube with a cuff, since the regulation procedure of the inner pressure and the measurement of the inner pressure are carried out separately, the using of these tubes are not easy and very complicated. To solve said problem, a device that can carry out simultaneously the regulation of inner pressure of cuff and the measurement of the inner pressure of cuff is developed. For example, a method to place a flat balloon between an air introduction hole and a tracheostomy tube or a endotracheal tube and to indicate the inner pressure of cuff by observing the inflation degree of the balloon, or a method to connect a tube for pressing between an air introduction hole and a tracheostomy tube or a endotracheal tube and to indicate the inner pressure of cuff are developed.

However, in the cases of these devices for indicating inner pressure of cuff, since the inner pressure is not displayed by numerical value, the accurate regulation of the inner pressure can not be expected. The increment and the reduction of the inner pressure by observing the inflation degree of balloon is a very difficult and complicated work, further the structure of the device becomes very complicated and needs electric source, and still more have a problem of rising the price of these devices.

BRIEF ILLUSTRATION OF THE INVENTION

The object of this invention is to provide an inner pressure indicator of cuff attached to a tracheostomy tube with a cuff or an endotracheal tube with a cuff, characterizing by a simple structure, cheap, compact, easy handling, further said inner pressure indicator has also a function to increase or reduce the inner pressure of a cuff by observing the indicated value of the inner pressure of cuff.

The present invention is an inner pressure indicator of cuff comprising, a housing possessing on one end an opening that can connect to a cuff inflating tube of a tracheostomy tube with a cuff or of an endotracheal tube with a cuff and on the other end of said housing an opening to which a valve that prevent the reduction of inner pressure is equipped with, said housing is characterized by being equipped with an inner pressure indicating device of cuff and also the inner pressure of the cuff can be regulated by said opening with a valve by way of said inner pressure indicating device of cuff.

The structural feature of an inner pressure indicator of cuff of a tracheostomy tube with a cuff or an endotracheal tube with a cuff of this invention can be illustrated as follows. That is, one end of said indicator is connected to an inflating tube of a tracheostomy tube with a cuff or an endotracheal tube with a cuff, and an opening with a valve that can prevent the reduction of inner pressure of the cuff at another end. The regulation of inner pressure of cuff is carried out by the opening with a valve by way of the inner pressure indicating device of the cuff contained in a housing, therefore the degree of pressurization or decompression can be indicated by the inner pressure indicator.

Figure 1:
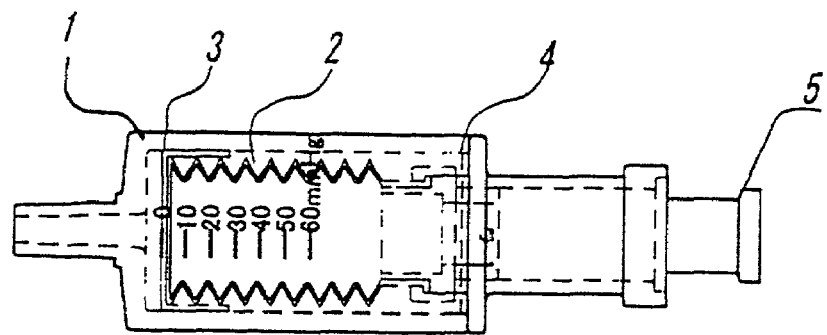
FIG. 1 is a structural feature of the inner pressure indicator of a tracheostomy tube with a cuff of this invention.

In the drawings, each numerical marks indicates,

1: Housing, 2: Bellows structure that indicates inner pressure of cuff, 3: Bellows structure cap, 4: Branch cap, 5: Seal valve (opening) 6: Lock part, 7: Bellows structure, 8: Bellows structure cap, 9: Seal valve intermediate part, 10: Seal valve, 11: Spring, 12: cuff, 13: Balloon (connector), 14: Inflation tube, 15: Neck plate

DETAILED ILLUSTRATION OF THE INVENTION

The detail of the present invention is illustrated as follows.

In the present invention, a tracheostomy tube with a cuff or an endotracheal tube with a cuff on one end means a conventional tracheostomy tube with a cuff or an endotracheal tube with a cuff, and an indicator is connected to the cuff inflation tube of said conventional tracheostomy tube with a cuff or an endotracheal tube with a cuff. At the opposite end of the indicator, there is an opening with a valve. The kind of valve is not restricted, however, for example, a syringe is desirably used. The syringe is connected to the opening and the inner pressure of the cuff can be adjusted to the desired pressure level by pressurizing or decompressing action of the syringe. Said action of the syringe can be carried out simultaneously with the observation of the indicated inner pressure value by the indicator.

As an inner pressure indicating device of a cuff equipped with the housing, it is desirable to arrange an elastic mechanism in the housing and to indicate the degree of elasticity of said elastic mechanism by numerical value. As the concrete example of an elastic mechanism, a bellows structure or a spring structure that can indicate the inner pressure of cuff by the elastic action of these structure. Especially, it is desirable to indicate the elastic action of said bellows or spring structure or a combined structure of them by a scale printed at the surface of the housing, because it is easier.

Further, on the opening to which a syringe is connected a seal valve is equipped with. Said seal valve can prevent the air leak of a cuff and even if in the case that the syringe is removed it maintains the inner pressure of the cuff as is. In the case that the inner pressure of the cuff is too high, a syringe can be connected to afore mentioned opening so as the inner pressure to be reduce. And since said pressure regulation is carried out by way of the pressure indicating device, the inner pressure of the cuff can be known immediately.

Still more, it is possible to equip a lock mechanism with a pointed end of the housing for the purpose to make it sure the connection of the inner pressure indicator and the inflation tube. Concretely, the lock mechanism of an injection needle of syringe is usual and desirably used.

EXAMPLE

The present invention will be concretely illustrated with reference to the drawings, however, the drawings are intended to illustrate the invention and not to be construed to limit the scope of the invention.

Figure 2:
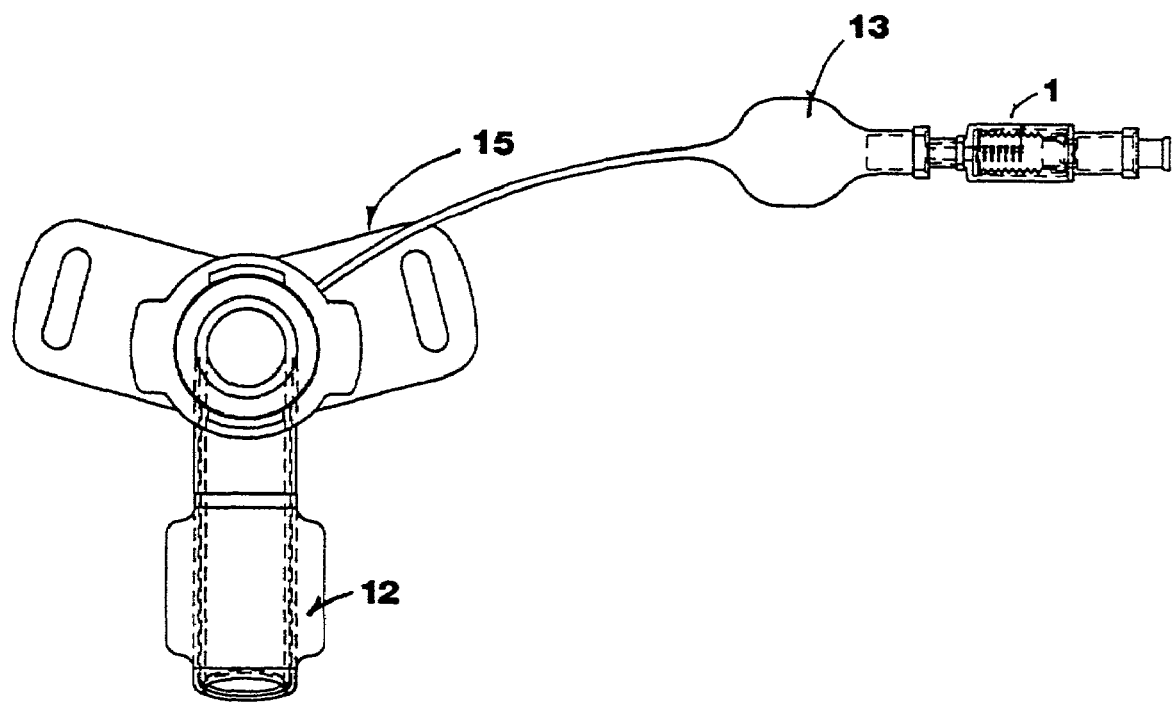
FIG. 2 shows the state that the inner pressure indicator of cuff is connected to a tracheostomy tube with a cuff of this invention.

FIG. 1 shows a structural feature of one embodiment of an inner pressure indicator of a cuff attached to a tracheostomy tube with a cuff or an endotracheal tube with a cuff, and FIG. 2 shows the connected state of an inner pressure indicator of a cuff to a tracheostomy tube with cuff.

The inner pressure indicator of a cuff of tracheostomy tube with a cuff or an endotracheal tube with a cuff of this invention is composed of a housing 1 to contain a device, a bellows structure 2 to indicate the inner pressure of cuff, a bellows structure cap 3 to hold said bellows structure, a branch cap 4 to make the air in bellows structure pass through and a seal valve 5 to prevent the air leak from the cuff. A spring structure can be added to the bellows structure. Said bellows structure is made of black colored material for the purpose that the numerical value of inner pressure can be easily read.

When the seal valve 5 is closed, the inner pressure of cuff press the front surface of the bellows structure, because the air in bellows structure 2 can pass through to the outside of indicator freely through the seal valve. The bellows structure 2 is shrunk by added pressure, and from the shrunk length of the bellows structure the inner pressure can be measured. At the actual use, it is desired that a bellows structure or a spring structure to have elasticity to shrink to the minimum size by the maximum inner pressure of 100–150 mmHg. Further, at the actual use of the inner pressure indicator, it is necessary to indicate inner pressure of 0–150 mmHg (in FIG. 1, 0–60 mmHg is indicated). And, especially the accurate gage pressure between 25 to 35 mmHg, which is the proper inner pressure of the cuff, is desired to be indicated precisely.

A housing 1 is made of transparent material so as the bellows structure 2 and bellows structure cap 3 contained in the housing to be seen through, and on the surface of the housing a scale is printed using numerical value or color display for the purpose to indicate the inner pressure of the cuff by the degree of shrinking of the bellows structure. Although the seal valve 5 is regularly closing the opening, by the insertion of a syringe the seal valve is pushed and opens the opening.

The method how to use the inner pressure indicator of cuff of a tracheostomy tube with a cuff or an endotracheal tube with a cuff is illustrated in FIG. 2. Namely, an opening of the housing 1 is connected to the inflation tube 14 of a tracheostomy tube with a cuff and another opening 5 with seal valve is connected to a syringe. The inside of cuff 12 is compressed by operating the syringe, and the inner pressure of the cuff can be measured by observing the numerical value or color display of the scale. If the inner pressure of cuff is too high, the inner pressure can be reduced by connecting again the syringe and opening the seal valve.

Figure 3:
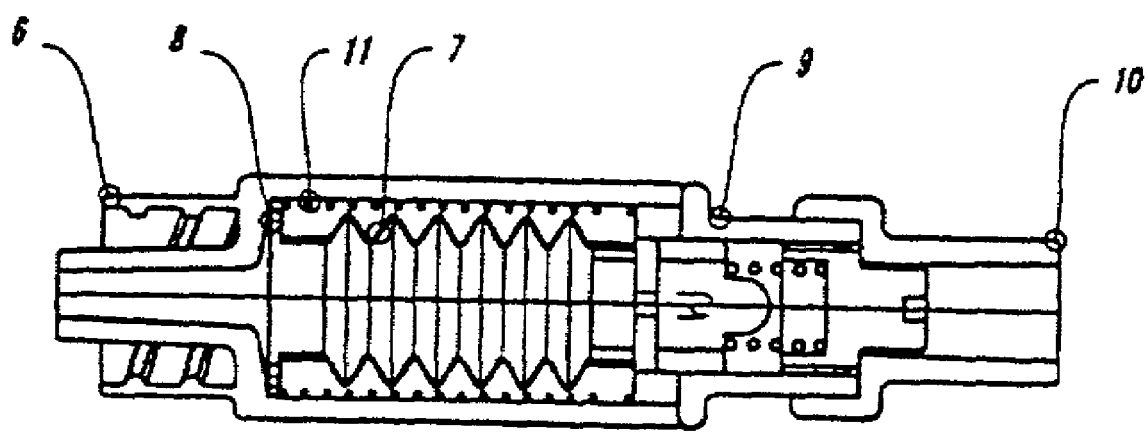
FIG. 3 is a cross sectional view of the inner pressure indicator of cuff with lock.
Figure 4:
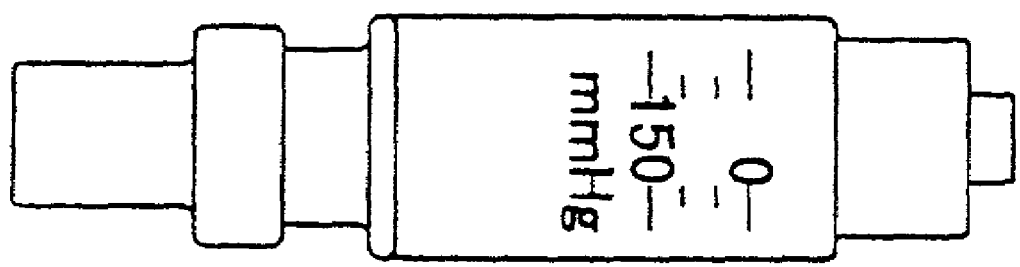
FIG. 4 is an external view of the inner pressure indicator of cuff with a lock.
Figure 5:
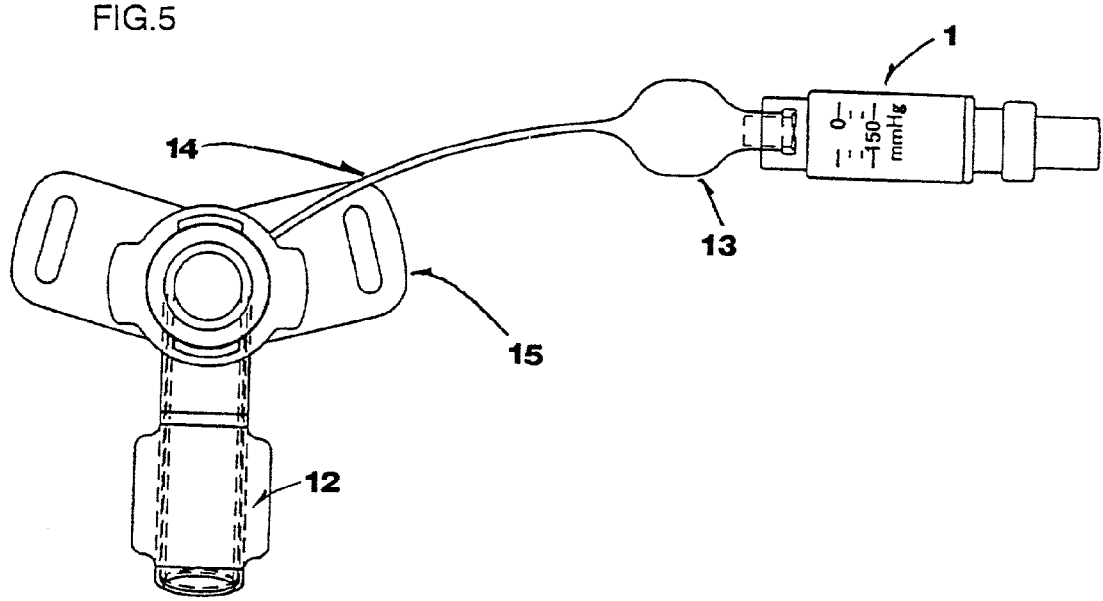
FIG. 5 shows the state that the inner pressure indicator of cuff with a lock is connected to a tracheostomy tube with a cuff.
Figure 6:
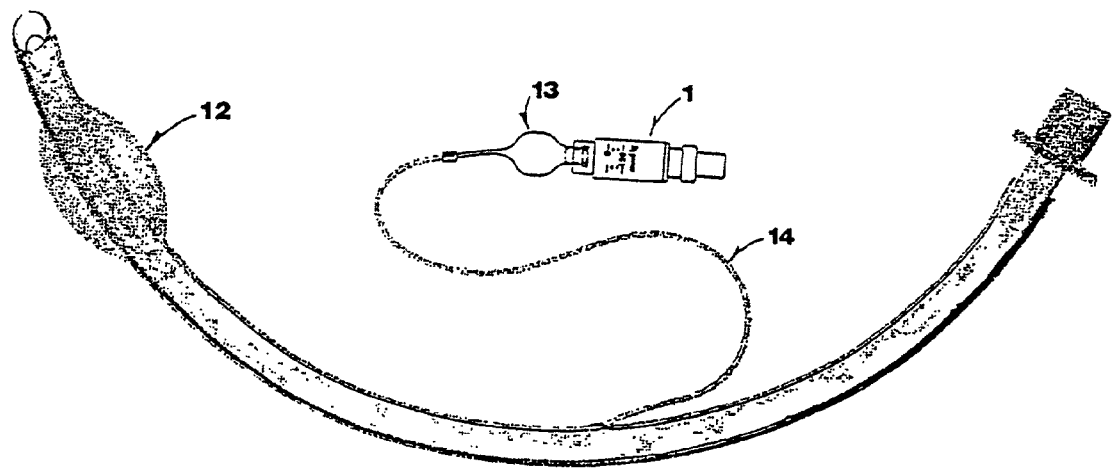
FIG. 6 shows the state that the inner pressure indicator of cuff with lock is connected to an endotracheal tube with a cuff.

FIGS. 3-6 are the drawings showing other embodiments of this invention. That is, FIG. 3 is a cross sectional view of the inner pressure indicator of cuff with a lock, FIG. 4 is an external view of the inner pressure indicator of cuff with a lock, FIG. 5 shows the state that the inner pressure indicator of cuff with lock is connected to a tracheostomy tube with a cuff and FIG. 6 shows the state that the inner pressure indicator of cuff with a lock is connected to an endotracheal tube with a cuff. In FIG. 3, at the end of the housing 1 is equipped with a lock mechanism 6 and to the another end point is equipped with a seal valve 10 putting a seal valve intermediate part 9. In the housing, a bellows structure 7 that indicates inner structure, and a bellows structure cap 8 that hold the bellows structure and make the readout of inner pressure easier are contained like to FIG. 1, and additionally a spring 11 is contained in the housing. As the indicating numerical value of the inner pressure, the scale from 0 to 150 mmHg is printed on the surface of the housing. In this case, the indication of inner pressure is carried out by the combination of the bellows structure and the spring. That is, the inner pressure of cuff is investigated by the bellows structure and the bellows structure is shrunk. The function of the spring is added to the shrinking action of bellows structure. By combining the spring to the bellows structure, the more accurate indication of the inner pressure that is difficult by the bellows structure alone becomes possible.

EFFECT OF THE INVENTION

The structural feature of the inner pressure indicator of cuff for a tracheostomy tube with a cuff or an endotracheal tube with a cuff of this invention is illustrated in detail as above. That is, the structural feature of the inner pressure indicator of this invention has a strong point of being compact and easy handling. Since the inner pressure indicator of a cuff of this invention can be used regulating the inner pressure of cuff by pressuring or decompressing action by observing the inner pressure value of the indicator, a tracheostomy tube with a cuff or an endotracheal tube with a cuff can be used without hurting the trachea of the patient.

What is claimed is:

1. An inner pressure indicator capable of indicating inner pressure of an inflatable cuff of a tracheostomy or endotracheal tube, said indicator comprising an elongated housing having an axis extending between one end having a first opening for connection to a cuff inflating tube, and an opposing end having a second opening to which is connected a valve whereby said inner pressure is regulated, wherein said housing is characterized by being equipped with an inner pressure indicating means comprising an in-line elastic bellows axially aligned with said axis, said bellows being within said housing and responsive to the inner pressure of said cuff exerting pressure thereon, said in-line bellows having a first closed end adjacent to said first opening and a structure cap over said first closed end, a second open end adjacent to said second opening, and a branch cap over said open end of said in-line bellows providing means whereby air within said bellows is permitted to pass freely outside of said housing in response to pressure from within said cuff exerted on said structure cap when said inner pressure of said cuff exceeds a prescribed pressure thereby expelling air from within said in-line bellows through said branch cap, and said valve is adapted to cooperate with a syringe whereby the inner pressure of said cuff is regulated through said housing by opening said valve whereby a constant reading of said inner pressure of said cuff is provided.

2. The inner pressure indicator of claim 1, wherein said valve is a seal valve.

3. The inner pressure indicator of claim 2 wherein said inner pressure indicating means further comprises a spring concentric with said in-line elastic bellows.

4. The inner pressure indicator of claim 3 further comprising indicia on said housing identifying the pressure within said cuff and characterized in that the inner pressure of a cuff to be indicated is from 0 to 150 mmHg.

5. The inner pressure indicator of claim 2 further comprising indicia on said housing identifying the pressure within said cuff and characterized in that the inner pressure of a cuff to be indicated is from 0 to 150 mmHg.

6. The inner pressure indicator of claim 1 further comprising indicia on said housing identifying the pressure within said cuff and characterized in that the inner pressure of a cuff to be indicated is from 0 to 150 mmHg.

* * * * *